US008032202B2

(12) United States Patent
Omi et al.

(10) Patent No.: US 8,032,202 B2
(45) Date of Patent: Oct. 4, 2011

(54) FUNCTION IMAGE DISPLAY METHOD AND DEVICE

(75) Inventors: Yasuo Omi, Chiba (JP); Osamu Miyazaki, Ibaraki (JP); Susumu Yasuda, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 1106 days.

(21) Appl. No.: 10/551,885

(22) PCT Filed: Apr. 2, 2004

(86) PCT No.: PCT/JP2004/004884
§ 371 (c)(1),
(2), (4) Date: Sep. 30, 2005

(87) PCT Pub. No.: WO2004/089218
PCT Pub. Date: Oct. 21, 2004

(65) Prior Publication Data
US 2006/0215889 A1 Sep. 28, 2006

(30) Foreign Application Priority Data

Apr. 4, 2003 (JP) ................................ 2003-101284
Oct. 3, 2003 (JP) ................................ 2003-345364

(51) Int. Cl.
*A61B 5/00* (2006.01)
(52) U.S. Cl. ......... 600/425; 600/407; 600/409; 382/128
(58) Field of Classification Search .................. 600/425, 600/427, 437–443; 382/128, 130, 131
See application file for complete search history.

(56) References Cited

U.S. PATENT DOCUMENTS

| 5,982,953 | A | 11/1999 | Yanagita et al. |
| 6,116,244 | A * | 9/2000 | Hossack et al. ............... 600/441 |
| 6,224,553 | B1 * | 5/2001 | Nevo ............................. 600/437 |
| 6,792,302 | B2 * | 9/2004 | Wintermark et al. ......... 600/407 |
| 2004/0096088 | A1* | 5/2004 | Kohle ........................... 382/128 |
| 2006/0173292 | A1* | 8/2006 | Baba et al. .................... 600/425 |

FOREIGN PATENT DOCUMENTS

JP 58-116343 7/1983
(Continued)

OTHER PUBLICATIONS

Dec. 7, 2009 Japanese official action in connection with a counterpart Japanese patent application No. 2005-505274.

*Primary Examiner* — Tse Chen
*Assistant Examiner* — Vani Gupta
(74) *Attorney, Agent, or Firm* — Cooper & Dunham LLP

(57) ABSTRACT

There are provided a function image display method and device capable of performing analysis of biological function information by acquiring from a single image, information obtained from a tomogram and information obtained from a plurality of function images without need of observing the plurality of function images and the tomogram by successively moving the eye line, and easily making judgment about the danger degree of the biological function abnormality.

A plurality of function images each displayed by a unique and arbitrary gradation color scale are combined with an arbitrary weight or an image obtained by calculating the inter-function images is displayed or these are combined with the tomogram with an arbitrary weight.

Furthermore, an operator can arbitrarily set and modify the range to which weight is applied, the range for displaying the gradation color scale, and the range to be combined.

21 Claims, 11 Drawing Sheets

FOREIGN PATENT DOCUMENTS

| | | |
|---|---|---|
| JP | 59-183459 | 10/1984 |
| JP | 3-132272 | 6/1991 |
| JP | 6-215150 | 8/1994 |
| JP | 8-77329 | 3/1996 |
| JP | 2001-212138 | 8/2001 |
| JP | 2003-70781 | 3/2003 |
| WO | WO01/57777 A2 | 8/2001 |
| WO | WO 2004024003 A1 * | 3/2004 |

* cited by examiner

Fig. 4

LUT FOR FUNCTIONAL IMAGE 1

| CONVERSION COEFFICIENT C | R | G | B |
|---|---|---|---|
| 0 | R1(0) | G1(0) | B1(0) |
| 1 | R1(1) | G1(1) | B1(1) |
| 2 | R1(2) | G1(2) | B1(2) |
| ⋯ | ⋯ | ⋯ | ⋯ |
| ⋯ | ⋯ | ⋯ | ⋯ |
| CMAX | R1(CMAX) | G1(CMAX) | B1(CMAX) |

LUT FOR FUNCTIONAL IMAGE 2

| CONVERSION COEFFICIENT C | R | G | B |
|---|---|---|---|
| 0 | R2(0) | G2(0) | B2(0) |
| 1 | R2(1) | G2(1) | B2(1) |
| 2 | R2(2) | G2(2) | B2(2) |
| ⋯ | ⋯ | ⋯ | ⋯ |
| ⋯ | ⋯ | ⋯ | ⋯ |
| CMAX | R2(CMAX) | G2(CMAX) | B2(CMAX) |

LUT FOR FUNCTIONAL IMAGE M

| CONVERSION COEFFICIENT C | R | G | B |
|---|---|---|---|
| 0 | RM(0) | GM(0) | BM(0) |
| 1 | RM(1) | GM(1) | BM(1) |
| 2 | RM(2) | GM(2) | BM(2) |
| ⋯ | ⋯ | ⋯ | ⋯ |
| ⋯ | ⋯ | ⋯ | ⋯ |
| CMAX | RM(CMAX) | GM(CMAX) | BM(CMAX) |

Rl ⋯MINIMUM COMPONENT R
Rh ⋯MINIMUM COMPONENT R
Gl ⋯MINIMUM COMPONENT G
Gh ⋯MINIMUM COMPONENT G
Bl ⋯MINIMUM COMPONENT B
Bh ⋯MINIMUM COMPONENT B
CMAX⋯MAXIMUM CONVERSION COEFFICIENT

LUT FOR TOMOGRAM

| CONVERSION COEFFICIENT C | R | G | B |
|---|---|---|---|
| 0 | 0 | 0 | 0 |
| 1 | 1 | 1 | 1 |
| 2 | 2 | 2 | 2 |
| ⋮ | ⋮ | ⋮ | ⋮ |
| ⋮ | ⋮ | ⋮ | ⋮ |
| ⋮ | ⋮ | ⋮ | ⋮ |
| CMAX | CMAX | CMAX | CMAX |

BEFORE THE THERAPY

AFTER THE THERAPY

COMPOSITE IMAGE OF CT IMAGE AND DIFFERENTIAL IMAGE OF BEFORE AND AFTER THE THERAPY

BEFORE THE THERAPY (CEREBRAL BLOOD VOLUME IMAGE)

AFTER THE THERAPY
(CEREBRAL BLOOD VOLUME IMAGE)

COMPOSITE IMAGE OF CT IMAGE AND
DIFFERENTIAL IMAGE OF BEFORE AND
AFTER THE THERAPY

FUNCTION IMAGE DISPLAY METHOD AND DEVICE This invention relates to analyzing and evaluating biological function data in an image diagnostic apparatus such as a CT apparatus or an MRI apparatus relying upon a tomogram obtained thereby.

BACKGROUND

In analyzing the biological function data, it is often attempted to totally diagnose a plurality of function data. In the analysis of cerebral perfusion function data, for example, the diagnosis is carried out, usually, by totally observing the data obtained from a plurality of functional images such as cerebral blood flow (CBF) image, cerebral blood volume (CBV) image, mean transit time (MTT) image, as well as data (e.g., early CT sign and anatomical impression such as running of blood vessels, positions of tissues, etc.) obtained from a tomogram.

An image display method for displaying biological function data has been disclosed in JP-A-2002-282248 wherein a piece of functional image is superposed on a tomogram and is displayed as apiece of composite image. According to this method, the data obtained from the tomogram and the data obtained from a functional image are displayed on a piece of image. A range of measurement is divided into a plurality of sections for each parameter of blood flow, blood volume and mean transit time, and different hues are allocated to the sections of measurement by using a color map. However, since only one parameter is displayed, it is difficult to totally recognize whether the biological function abnormality, symptom and danger are of light degrees or serious degrees (hereinafter referred to as danger degree). Besides, since color is displayed on the whole tomogram, the data are so complex that the abnormality cannot be easily judged.

As a method of observation by displaying a plurality of functional images obtained through examinations of a plurality of number of times, there has been proposed a method called SISCOM (subtracted ictal SPECT co-registered to MRI) by subtracting the SPECT (single photon emission computed tomography) images and composing a region where a distinct change is appearing on a standard brain MR image. This method is to obtain a functional image by subtracting SPECT images obtained, particularly, from an epileptic person during the ictal moment and the interictal moment. Here, an electrode-type electroencephalogram (EEG) is also used in combination. The above SISCOM is corresponding to the SPECT image only, but cannot be applied to the functional images formed from a CT image or an MR image. That is, when the tomograms obtained by different image diagnostic devices are overlapped one upon the other, unlike when the tomogram is obtained using a single image diagnostic device, it is necessary to transform the CT image or the MR image into a standard brain. However, it is difficult to bring the positions and the shapes into agreement. Besides, both the SPECT image and the MR image must be obtained, and the patient must be held locked for extended periods of time. Further, when the SPECT image and MR image are to be overlapped one upon the other, the SPECT image is deformed to meet the standard brain and is adjusted for its position with the MR image imposing a probability of losing the inherent shape of the patient's brain and of losing important data related to the shape. When the patient's skull is deformed, in particular, the loss of data of the shape becomes a serious problem.

SUMMARY

In an aspect of this disclosure, there is provided an apparatus for diagnosing image, which is capable of easily judging the danger degree by summarizing the data obtained from a tomogram and the data obtained from a plurality of functional images into a piece of image by using a single apparatus for diagnosing image (modality). For example, an apparatus and a method for diagnosing image, in an exemplary embodiment, includes displaying the data of a necessary portion only among the data in a plurality of required functional images, rendering the judgment free of confusion caused by complex data, and making it possible to efficiently judge the danger degree.

In an aspect of this disclosure, there is provided an apparatus and a method for diagnosing image, capable of analyzing biological function data by easily grasping a change in the biological functional data with the passage of time from a functional image formed based on the CT images or the MR images in the examinations of a plural number of times without losing the shape inherent in the region that is examined.

In another aspect of this disclosure, there is provided an apparatus and a method for diagnosing image, which is capable of objectively evaluating and analyzing the biological function data with the passage of time irrespective of a particular habit of an operator even when the same data are analyzed by a different operator.

In an aspect of this disclosure, there is provided an apparatus and a method for diagnosing image, which is capable of grasping and analyzing a change in the biological function data with the passage of time without using a plurality of modalities but using a modality of either a CT apparatus or an MR apparatus.

A first feature of this disclosure is concerned with an apparatus for displaying image comprising means for collecting image data of a person being examined, means for forming a tomogram from the image data, means for calculating at least one biological function data from the tomogram, means for forming at least one functional image based on the biological function data, means for forming composite image by composing said tomogram and at least one of the following images; an operated image obtained by operating said functional images together, a composite image obtained by composing said functional images together, said operated image, and said functional image; and display means capable of displaying the functional image, the operated image, the tomogram and the composite image, wherein the means for forming the functional image and the means for forming the composite image work to display at least portions of the regions in the functional image and in the operated image on an arbitrary gradation color scale corresponding to the evaluated value of the biological function data, and other regions in the functional image and in the operated image are displayed in an arbitrary color which is not included in the gradation color scale, or are displayed transparently.

A second feature of this disclosure resides in an apparatus for displaying image of the above first feature, wherein the composite image is displayed by any one of an overlapped display, a parallel display or a partial display.

A third feature of this disclosure resides in an apparatus for displaying image of the above first or second feature, wherein means for forming the functional image sets to zero the ratio of the functional image in other regions in the functional image.

A fourth feature of this disclosure resides in an apparatus for displaying image of the above first to third features, wherein means for forming the functional image is capable of arbitrarily varying the gradation color scale allocated to the biological functional data.

A fifth feature of this disclosure resides in an apparatus for displaying image of the above first to fourth features, wherein means for forming the composite image is capable of arbitrarily setting the ratios of the functional images in the composite images and of the tomogram.

A sixth feature of this disclosure resides in an apparatus for displaying image of the above first to fifth features, wherein means for forming the functional image specifies part of the regions in the functional image depending upon whether the image data value of the pixel unit lies inside or outside a predetermined range.

A seventh feature of this disclosure resides in an apparatus for displaying image of the above first to sixth features, wherein means for forming the functional image determines an arbitrary region of interest in the functional image as part of the region in the functional image.

An eighth feature of this disclosure resides in an apparatus for displaying image of the above first to sixth features, wherein means for forming the functional image renders the pixel values of the pixels of the image data on a predetermined window level and in a predetermined window width to be corresponded to conversion coefficients, and determines the gradation color scale based on the conversion coefficients.

A ninth feature of this disclosure resides in an apparatus for displaying image of the above first to eighth features, wherein means for forming the functional image determines the gradation color scale allocated to the functional image depending upon the pixel values of the pixels of the image data for each of RGB and upon various look-up tables to which the conversion coefficients are corresponded.

A tenth feature of this disclosure resides in an apparatus for displaying image of the above first to ninth features, wherein the biological function data is at least one of the blood flow function data as represented by blood volume, blood flow and mean transit time.

An eleventh feature of this disclosure is concerned with a method of displaying image comprising a step of collecting image data of a person being examined, a step of forming a tomogram from the image data, a step of calculating at least one biological function data from the tomogram, a step of forming at least one functional image based on the biological functional data, a step of forming a composite image by composing said tomogram and at least one of the following images; an operated image obtained by operating said functional images together, a composite image obtained by composing said functional images together, said operated image, and said functional image; and a display step capable of displaying the functional image, the operated image, the tomogram and the composite image, wherein the step of forming the functional image and the step of forming the composite image work to display at least portions of the regions in the functional image and in the operated image on an arbitrary gradation color scale corresponding to the evaluated value of the biological functional data, and other regions in the functional image and in the operated image are displayed in an arbitrary color which is not included in the gradation color scale, or are displayed transparently.

A twelfth feature of this disclosure resides in a method of displaying image of the above eleventh feature, wherein the composite image is displayed by any one of an overlapped display, a parallel display or a partial display.

A thirteenth feature of this disclosure resides in a method of displaying image of the above eleventh to twelfth features, wherein the step of forming the functional image sets to zero the ratio of the functional image in other regions in the functional image.

A fourteenth feature of this disclosure resides in a method of displaying image of the above eleventh to thirteenth features, wherein the step of forming the functional image is capable of arbitrarily varying the gradation color scale allocated to the biological function data.

A fifteenth feature of this disclosure resides in a method of displaying image of the above eleventh to fourteenth features, wherein the step of forming the composite image is capable of arbitrarily setting the ratios of the functional images in the composite images and of the tomogram.

A sixteenth feature of this disclosure resides in a method of displaying image of the above eleventh to fifteenth features, wherein the step of forming the functional image specifies part of the regions in the functional image depending upon whether the image data value of the pixel unit lies inside or outside a predetermined range.

A seventeenth feature of this disclosure resides in a method of displaying image of the above eleventh to sixteenth features, wherein the step of forming the functional image determines an arbitrary interested region in the functional image as region of interest in the functional image.

An eighteenth feature of this disclosure resides in a method of displaying image of the above eleventh to seventeenth features, wherein the step of forming the functional image renders the pixel values of the pixels of the image data on a predetermined window level and in a predetermined window width to be corresponded to conversion coefficients, and determines the gradation color scale based on the conversion coefficients.

A nineteenth feature of this disclosure resides in a method of displaying image of the above eleventh to eighteenth features, wherein the step of forming the functional image determines the gradation color scale allocated to the functional image depending upon the pixel values of the pixels of the image data for each of RGB and upon various look-up tables to which the conversion coefficients are corresponded.

A twentieth feature of this disclosure resides in a method of displaying image of the above eleventh to nineteenth features, wherein the biological function data is at least one of the blood flow function data as represented by blood volume, blood flow and mean transit time.

BRIEF DESCRIPTION OF THE DRAWINGS

FIG. 4 is a diagram illustrating the constitutions of look-up tables for functional images;

BEST MODE FOR CARRYING OUT THE INVENTION

Preferred embodiments of the method and apparatus for displaying functional image according to the present invention will now be described with reference to the accompanying drawings.

Embodiment 1

Figure 1:
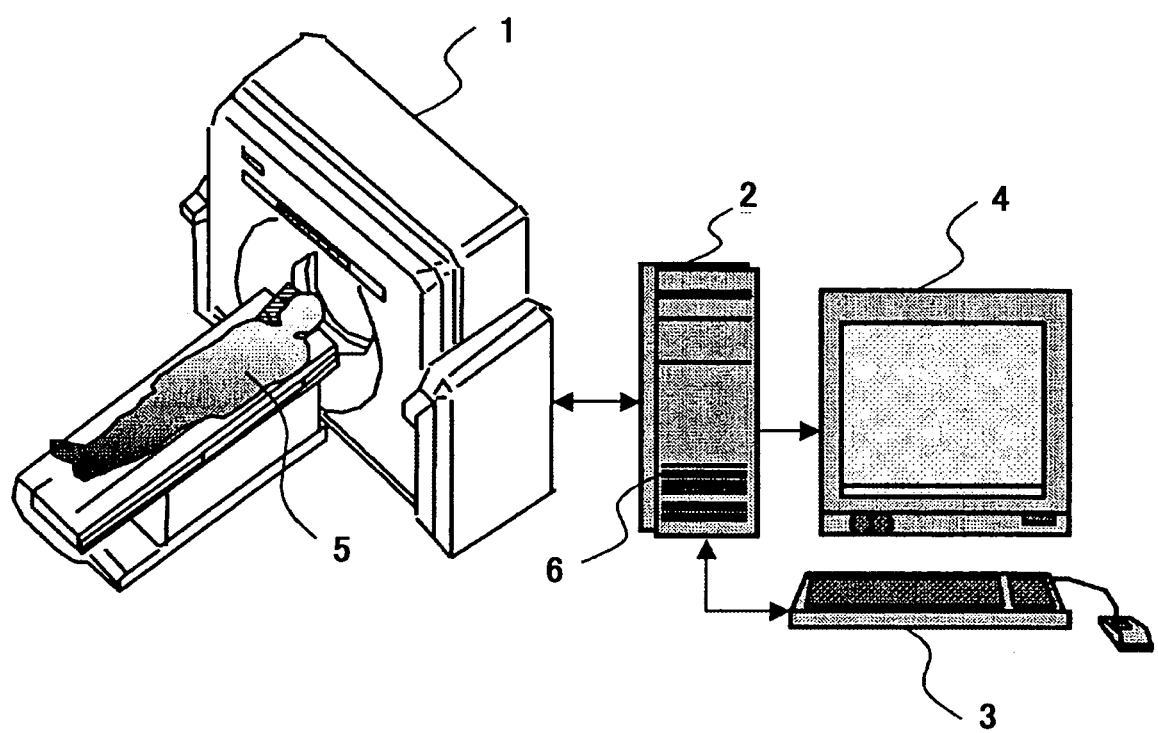
FIG. 1 is a view of constitution illustrating a method of displaying functional image and an apparatus of the invention.

FIG. 1 is a view illustrating a method and an apparatus for displaying a functional image according to a preferred embodiment of the invention. The method and the apparatus for displaying a functional image of the invention comprises means 1 for collecting tomogram data such as X-ray attenuation signals and echo signals emitted from nuclear magnetic resonance, such as CT apparatus or MRI apparatus, a computer 2 for controlling the acquisition means 1 and for executing various operations, a console 3 such as a mouse or a keyboard, and display means 4 such as a display. The computer 2 is mounting a program for controlling the acquisition means 1, a program for forming a tomogram, such as reconstituting the image, a program for analyzing and mapping the biological function data, and a program for forming a composite image. In constituting the method and apparatus for displaying functional image according to the present invention, the above programs may be mounted in one computer or may be mounted in a divided manner in a plurality of computers depending upon the kinds of operations.

Figure 2:
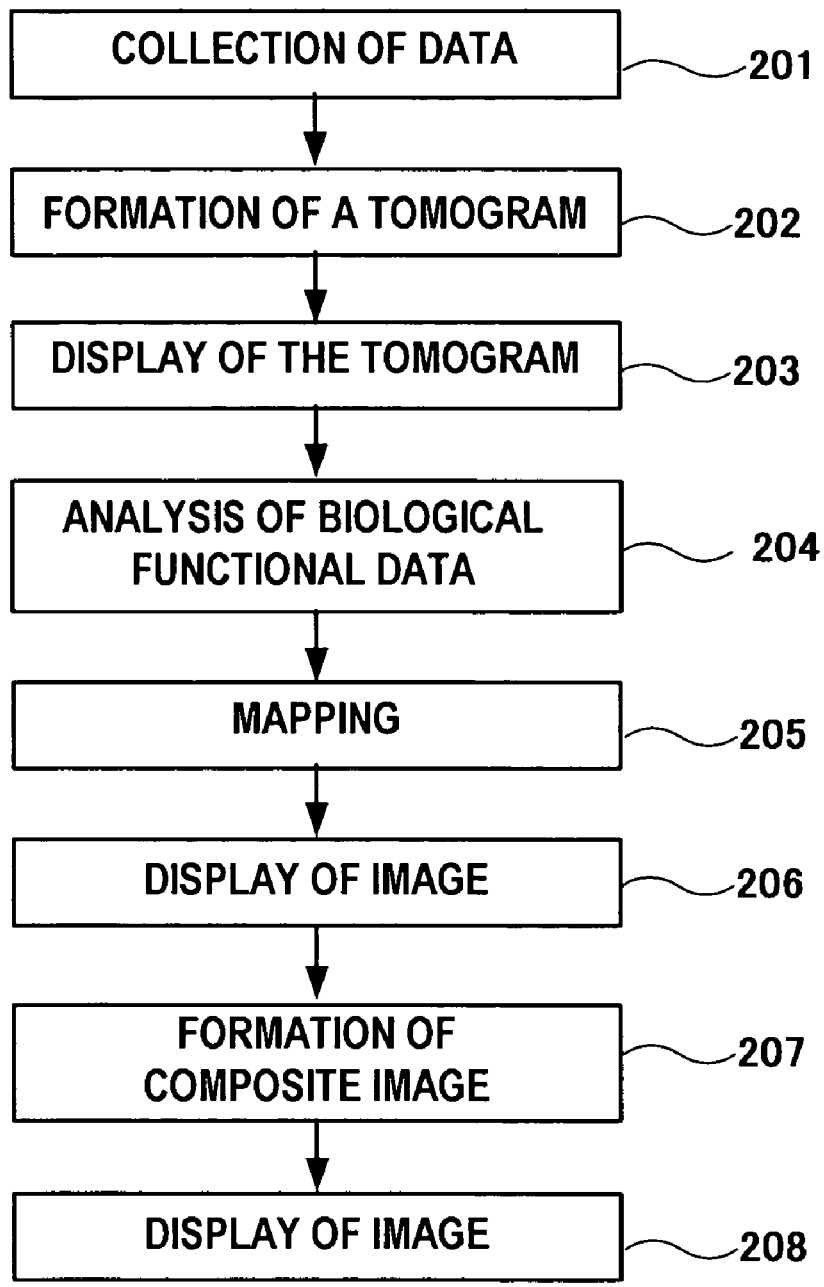
FIG. 2 is a flowchart from collecting the data through up to displaying the composite image.

FIG. 2 is a flowchart from collecting the data through up to displaying a composite image in the method and the apparatus for displaying function image according to the invention. This flowchart is realized by a software incorporated in the computer 2 of FIG. 1 or incorporated in an external computer that is not shown.

The embodiment will now be described in line with the flowchart. First, acquisition means 1 controlled by a control program mounted on the computer 2, works to collect the X-ray attenuation data and susceptibility signal intensity data (step 201).

At step 201, acquisition means 1 controlled by a control program on the computer 2 collects X-ray attenuation signals and echo signals emitted from nuclear magnetic resonance. When, for example, the data acquisition apparatus is a CT apparatus, and the biological function data to be analyzed are perfusion data of the brain tissue, a contrast emphasizing tracer such as an iodine-type contrast medium is injected to a patient 5, and a particular organ or a portion into which the above substance flows is imaged in a same section (so-called dynamic imaging) with the passage of time to collect the data necessary for the analysis of the biological function data.

At step 202, a tomogram is formed by using a program such as reconstituting the image mounted on the computer 2.

At step 203, the tomogram formed at step 202 is displayed. At step 204, a parameter representing the biological functional data, i.e., a pixel value P is calculated by using a program for analyzing the biological function data mounted on, for example, the computer 2. Representative examples of the parameter referred to here include a cerebral blood flow (CBF) image, a cerebral blood volume (CBV) image and a mean transit time (MTT) image.

It is desired that the parameter is calculated for each pixel of the tomogram to prevent a decrease in the resolution. However, when it is forced to finish the operation within a short period of time such as quickly diagnosing the biological function data, the operation may be executed while reducing the image or the operation may be executed for each of the pixels.

At step 205, a function image is formed by mapping the results of operation obtained at step 204 by using a mapping program mounted on the computer 2.

At step 206, the functional image formed at step 205 is displayed on display means 4. At step 206, not only the functional image is displayed but, as required, the functional image and the tomogram may be displayed together. When the composite image is to be continuously formed, the image may not be displayed, here.

At step 207, a composite image is formed by using a program for forming composite image mounted on the computer 2 as will be described later.

At step 208, the composite image is displayed on the display means 4. Here, at step 208, in addition to displaying the image, there may, as required, be displayed at least two of the composite image, functional image and tomogram together.

When the X-ray attenuation data and the susceptibility signal intensity data have been collected already concerning the flowchart of FIG. 2, the X-ray attenuation data and the susceptibility signal intensity data are readout from storage means 6 such as a hard disk contained in the computer 2 or attached to the outer side thereof and, thereafter, step 202 and subsequent steps may be executed.

Further, when a tomogram has been formed already concerning the flowchart of FIG. 2, the tomogram is read out from storage means 5 such as the hard disk incorporated in the computer 2 or attached to the outer side thereof and, thereafter, step 203 and subsequent steps may be executed.

Further, when a functional image has been formed already concerning the flowchart of FIG. 2, the functional image is read out from storage means 5 such as the hard disk incorporated in the computer 2 or attached to the outer side thereof or, as required, the functional image and the tomogram are read out therefrom and, thereafter, step 206 and subsequent steps may be executed.

Next, described below is a method of forming a composite image at step 207. In this embodiment, the description is based on that there are a total of M kinds of biological function data, i.e., M pieces of functional images of an organ.

Further, the number of gradations is a positive integer, such as 8 bits (256 gradations), 12 bits (4,096 gradations), 16 bits (65,536 gradations) or 32 bits (4,294,967,296 gradations).

Hereinafter, the color tone stands for a hue, a chroma, a brightness, or a combination of at least two of them. Further, the color gradation scale stands for a continuity of color gradations obtained by dividing a range between a maximum pixel value and a minimum pixel value into at least one or more steps, and allocating different color tones to the steps.

(1) Conversion of a Pixel into a Conversion Coefficient.

Figure 3:
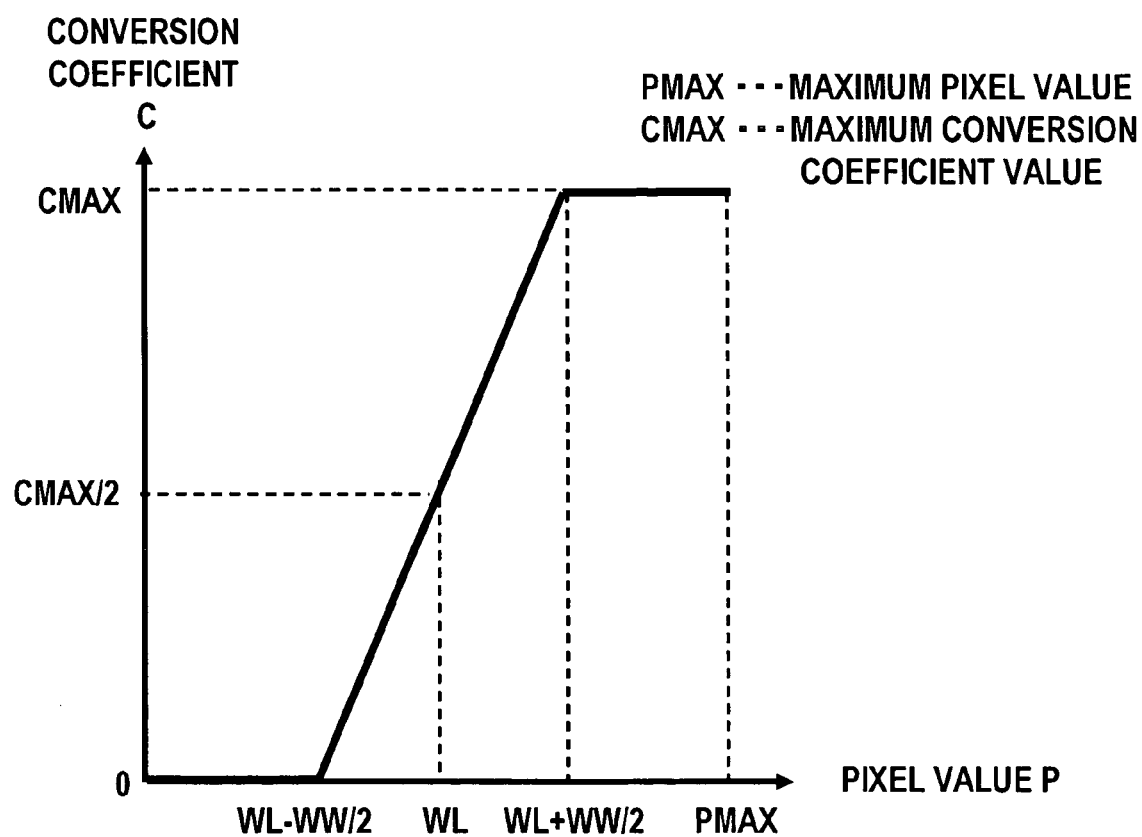
FIG. 3 is a diagram illustrating how to calculate conversion coefficients.

Described below is what is called a blended functional image. The blended functional image is obtained by the composite of overlapping a plural pieces of functional images displaying biological function data so as to be corresponded to the color gradation scales. Here, different color tones are used depending upon the functional images. Some of the functional images which are the initial images of the blended functional image may include those in which particular regions only are displayed by a given color gradation scale in the images. In this case, the regions other than the particular region may be displayed in any particular color. In forming a blended functional image, a conversion coefficient C is calculated based on a pixel value P of the functional image, a display window value WL and a display window width WW. Referring to FIG. 3, the conversion coefficient C is found according to the following formula 1. Here, WL is a window level and WW is a window width. The concentration that is displayed is allocated to upper and lower WW/2 ranges with the window level as a center. On the outer side of the range WW, there is no concentration or there is no change caused by the saturation. That is, in the regions where the pixel values are greater than the displayed window width WW, the concentration is saturated to appear white. On the other hand, the regions where the pixel values are small appear to be darkest. Further, PMAX represents a maximum pixel value and CMAX represents a maximum conversion coefficient.

$$P \le (WL - WW/2) \quad\quad C = 0 \quad\quad\quad (1)$$
$$(WL - WW/2) \le P \le (WL + WW/2) \quad C = CMAX/WW \cdot P$$
$$(WL + WW/2) \le P \quad\quad C = CMAX$$

In the embodiment shown in FIG. 3, a section from (WL−WW/2) to (WL+WW/2) was linearly converted, which, as required, however, may be non-linearly converted arbitrarily. It can further be considered to use the pixel value P as the conversion coefficient C.

FIG. 4 illustrates look-up tables (hereinafter abbreviated as LUTs) used for forming a blended functional image. The LUT referred to in this embodiment is a correspondence table between the conversion coefficient C described above and the components (e.g., component R, component G, component B) of the displayed color. The conversion coefficient C fitted to the pixels of the region smaller than (WL−WW/2) is the darkest color (lower end color) at an end of the color gradation scale. Hereinafter, the darkest colors of R, G and B for color display are represented by Rl, Gl and Bl. When allocated to the steps of the color gradation scale by varying the hue only in the color tone, it often happens that a color that appears to be the darkest is not necessarily allocated to the darkest color portion. Even in such a case, however, the color is called the darkest color (lower end color) for convenience.

On the other hand, the conversion coefficient C to be fitted to the pixels in a region where the value of the conversion coefficient C is greater than (WL+WW/2) exists at the other end of the color gradation scale and is the brightest color (upper end color). Hereinafter, the brightest colors (upper end colors) of R, G and B for displaying color are denoted by Rh, Gh and Bh. When allocated to the steps of the color gradation scale by varying the hue only in the color tone, it often happens that a color that appears to be the brightest is not necessarily allocated to the brightest color portion. Even in such a case, however, the color is called the brightest color (upper end color) for convenience.

Figure 5A:
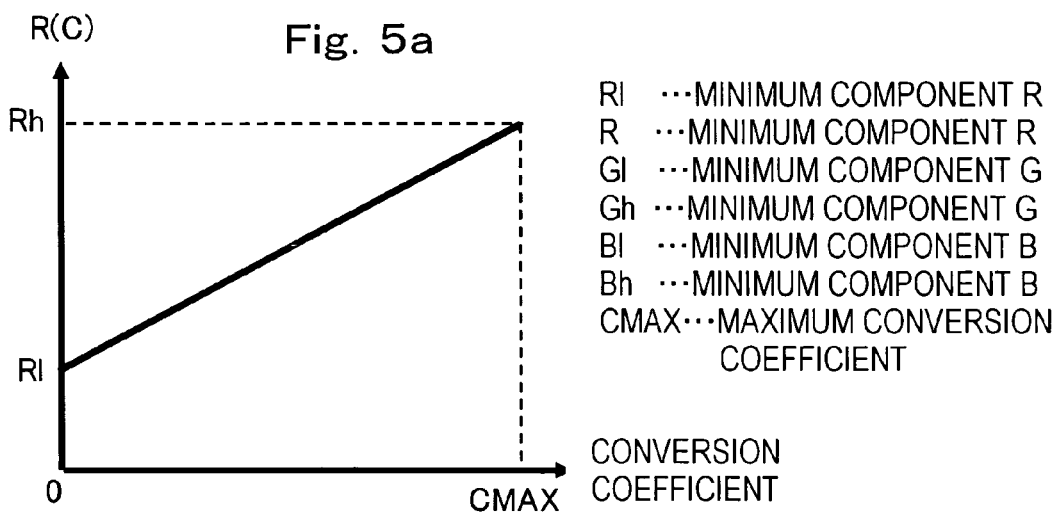
FIG. 5 is a diagram illustrating look-up tables for functional images.
Figure 5B:
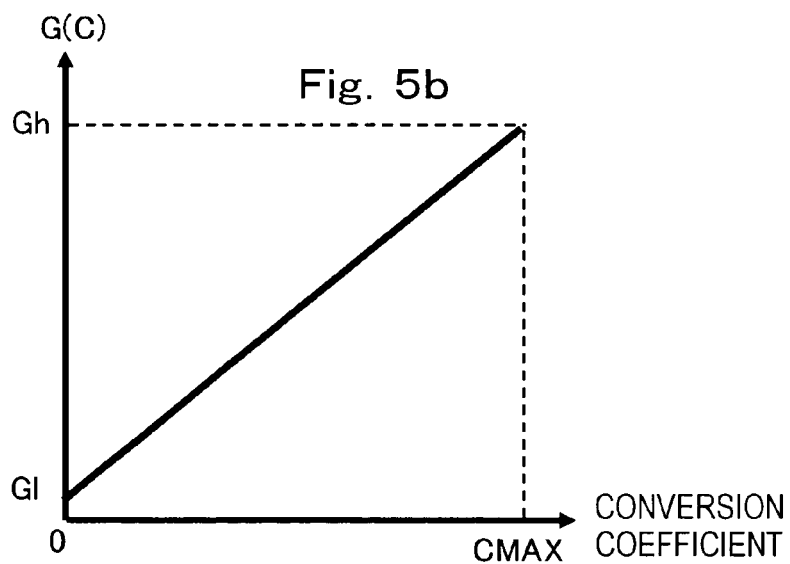
Figure 5C:
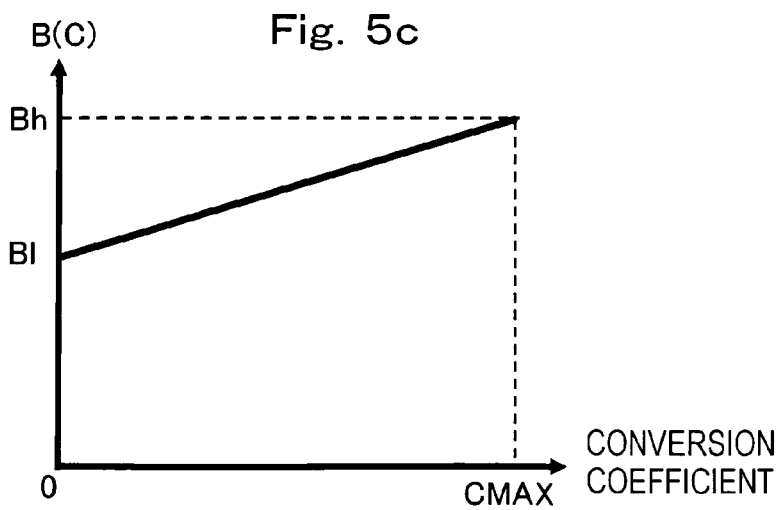

The components R(C), G(C) and B(C) of RGB in the LUT using a given conversion coefficient C may be determined according to the following formula (2) by making reference to the LUT for functional images as shown in, for example, FIG. 5. FIG. 5 illustrates LUTs of the colors RGB. Usually, the initial values and inclinations of tables of RGB allocated for each of the functional images are not the same. A system of a color for expressing the biological function data is determined depending upon a combination of the darkest colors R1, G1 and B1 which are the initial values of RGB.

$$R(C) = \frac{Rh - Rl}{CMAX} \cdot C + Rl \quad\quad (2)$$
$$G(C) = \frac{Gh - Gl}{CMAX} \cdot C + Gl$$
$$B(C) = \frac{Bh - Bl}{CMAX} \cdot C + Bl$$

In the example shown in FIG. 5, the components from the darkest color to the brightest color were connected together linearly, which, however, may be connected in any non-linear shape, as required. When there are M pieces of functional images, it is desired to set look-up tables of a number of M corresponding to a functional image 1, a functional image 2, - - -, a functional image M, i.e., to set LUT1, LUT2, - - -, LUTM. Not being limited thereto only, however, there may be used the same one for the plurality of functional images.

(2) Forming a Blended Functional Image.

Described below is how to handle the display image on a portion where a plurality of functional images are overlapped. Here, if the components R, G and B that affect the display color of a pixel (i, j) in a blended functional image are denoted by RF(i, j), GF(i, j) and BF(i, j), then, these components are determined according to the following formula 3, $$RF(i, j) = \frac{\sum_{k=1}^{m} R_k(C_k(i, j)) \cdot W_k}{\sum_{k=1}^{N} W_k} \quad\quad (3)$$

$$GF(i, j) = \frac{\sum_{k=1}^{m} G_k(C_k(i, j)) \cdot W_k}{\sum_{k=1}^{N} W_k}$$

$$BF(i, j) = \frac{\sum_{k=1}^{m} B_k(C_k(i, j)) \cdot W_k}{\sum_{k=1}^{N} W_k}$$

Here, Wk is a weight (distribution) for composing a plurality of functional images, and Ck(i, j) is a conversion coefficient of a functional image k in a pixel (i, j). Further, Rk(Ck(i, j)), Gk(Ck(i, j) and Bk(Ck(i, j)) are the component values of R, G and B specified by the LUTk using a conversion coefficient Ck(i, j), and are calculated by inputting the conversion coefficient Ck(i, j) for each of the pixels to the conversion coefficient C in the formula 2. Here, particularly, the number k of kinds of the functional images is an integer of from 1 to M as described earlier.

The region for display on the gradation color scale may be the whole image or a portion of the image. When only a portion of the image, i.e., a particular region only is to be displayed on the gradation color scale, it may be set depending on at least any one of the threshold value, the range or the ROI via the console 4. The threshold value, range and ROI may be set in a number of one or in a plural number for each kind of the functional images (process 1).

When a pixel (i, j) of a given functional image k is just representing a biological function, i.e., when the pixel (i, j) is in the ROI or, when, the pixel value is in a range determined by a threshold value for a functional image k, the components Rk(Ck(i, j)), Gk(Ck(i, j)) and Bk(Ck(i, j)) are determined according to the LUTk of FIG. 4 mentioned above. When the pixel value and the pixel are corresponding to none of the threshold value, range or range of ROI as described above, the particular values are allocated to the components Rk(Ck(i, j)), Gk(Ck(i, j)) and Bk(Ck(i, j)) to display in a particular color without hindering the display of a desired function (process 2).

The process 1 and the process 2 are effected for the whole pixels, so that a given function image is displayed on the gradation color scale in the above preset range only and is displayed in a particular color in other ranges. The process 1 and the process 2 may be effected for all functional images or may be effected for some functional images only.

Described below is the composite of the functional images by effecting the process 1 and the process 2. The functional images that are composed are hereinafter referred to as a blended functional image. The data of the blended functional image are obtained for each of the pixels. RF(i, j), GF(i, j) and BF(i, j) are determined for each of the pixels according to the formula 3. Here, the pixels displayed in the particular color are calculated by setting the weight Wk of the functional image to 0. When the data RF(i, j), GF(i, j) and BF(i, j) are obtained for all pixels, the image is displayed by mapping according to the coordinate (i, j). The blended functional image is thus formed. When there is no need of composing all of N pieces of functional images, the composite may be effected by setting the weight to 0 for those functional images that need not be composed. Though the threshold value, range and ROI were exemplified as the setting of particular ranges, there may be set any other parameters depending upon the requirement.

(3) Forming a Blended Function Image Projected onto a Tomogram.

Next, described below is how to form a composite image by overlapping the blended functional image on a tomogram (hereinafter called a blended function image projected onto the tomogram). Here, the components of a displayed color of a pixel (i, j) of a blended functional image projected onto the tomogram are denoted by RTF(i, j), GTF(, j) and BTF(i, j). These components can be determined as expressed by the following formula 4 by using the color components RF(i, j), GF(i, j) and BF(i, j) of each pixel in the blended functional image found by the above formula 3, by using a conversion coefficient CC(i, j) of the tomogram in the pixel (i, j), by using color component values RT(CC(i, j)), GT(CC(i, j)) and BT(CC(i,j)) found for the conversion coefficient CC(P) being corresponded to a plurality of look-up tables LUTT for tomogram discriminated by symbol t, and by using weights WB and WT of the blended functional image and of the tomogram.

$$RTF(i, j) = \frac{RF(i, j) \cdot WB + RT(CC(i, j)) \cdot WT}{WB + WT}$$

$$GTF(i, j) = \frac{GF(i, j) \cdot WB + GT(CC(i, j)) \cdot WT}{WB \cdot WT}$$

$$BTF(i, j) = \frac{BF(i, j) \cdot WB + BT(CC(i, j)) \cdot WT}{WB + WT}$$

(4)

Figures 6, 7:
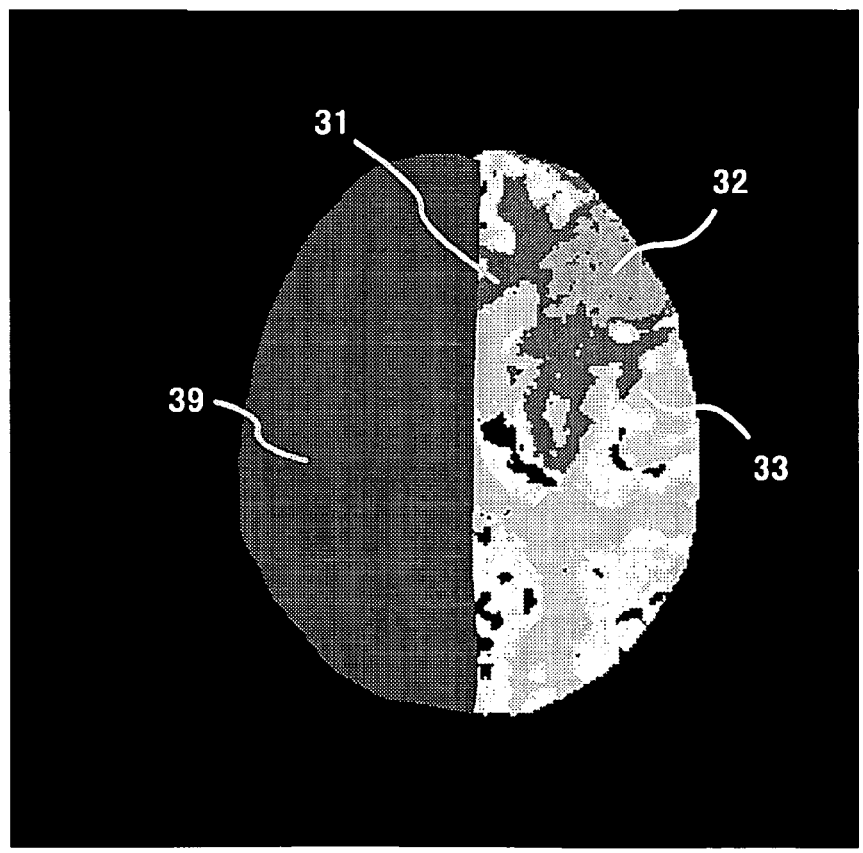
FIG. 6 is a diagram illustrating the constitution of a look-up table for tomogram.
FIG. 7 is a sample image which is a blended functional image.

A tomogram is, usually, displayed on a gray scale and, hence, a look-up table LUTT for a tomogram may be set as shown, for example, in FIG. 6. To form a blended functional image projected on the tomogram, RTF(i, j), GTF(i, j) and BTF(i, j) are determined according to the formula 4 when the pixels are displayed on the gradation color scale, and the pixels displayed in the particular color are determined for their RTF(i, j), GTF(i, j) and BTF(i, j) by setting the weight WB to 0 in the formula 4. If this is done for all pixels and is mapped, a blended functional image is completed being projected onto the tomogram.

In the blended image or in the blended functional image projected onto the tomogram, when it is desired to vary the gradation color scale of a given functional image k, Rk(Ck(i, j)), Gk(Ck(i,j) and Bk(Ck(i, j)) in the above formula 3 may be varied by varying the look-up table LUTk corresponding to the functional image based on a parameter input from the console 4 according to the method described above. Here, k is an integer of 1 to m.

In the blended image and in the blended functional image projected onto the tomogram, when it is desired to vary the degree of emphasis of data obtained from a given functional image k, Wk in the above formula 3 may be varied based on the parameter input from the console 4.

In the blended image and in the blended functional image projected onto the tomogram, when it is desired to vary the region displayed on the gradation color scale, parameters such as threshold value, range and ROI specifying the region may be varied by being input through the console 4.

In the blended functional image projected onto the tomogram, when it is desired to vary the degree of emphasis of the blended functional image, WB and WT in the formula 4 may be varied based on the parameters input from the console 4.

Figure 8:
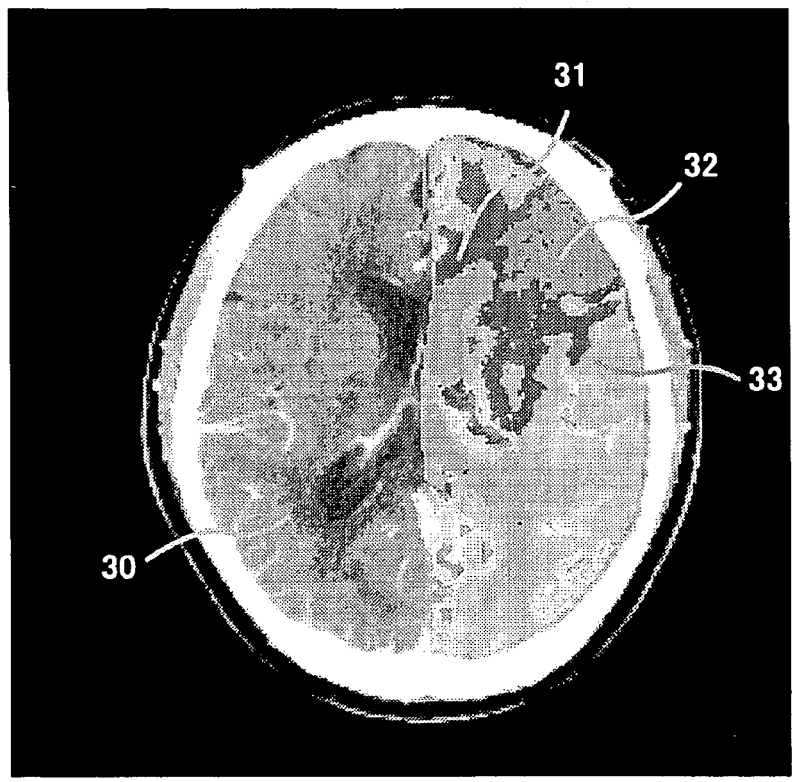
FIG. 8 is a sample image which is a blended functional image projected onto a tomogram.

FIGS. 7 and 8 illustrate examples where the embodiment of the invention is applied to cerebral blood flow functional images formed from a CT image. FIG. 7 shows a sample image which is a blended functional image formed from three kinds of function data (cerebral blood flow, cerebral blood volume, mean transit time), and is a composite image of a region 31 where the cerebral blood flow is abnormal, a region 32 where the cerebral blood volume is abnormal, a region 33 where the mean transit time is abnormal, and other regions 39. FIG. 8 shows a sample image which is a blended functional image projected onto a tomogram, and is formed from a CT image 30 and a blended functional image of three kinds of function data (cerebral blood flow, cerebral blood volume, mean transit time). In these sample images, the region 31 where the cerebral blood flow is abnormal is displayed on a green gradation color scale, the region 32 where the cerebral blood volume is abnormal is displayed on a blue gradation color scale, and the region 33 where the mean transit time is abnormal is displayed on a red gradation color scale. These sample images are not only displaying, on a piece of image, the regions where biological parameters appear to be abnormal in the cerebral blood flow, cerebral blood volume and mean transit time but are also indicating danger degree of abnormal conditions depending upon the concentration of coloring and the mixing of colors, from which the effect of the present invention will be comprehended. There can be obtained not only one kind of the blended functional image and the blended functional image projected onto the tomogram, but also a plurality of different blended functional images and blended functional images projected onto the tomogram by selectively composing some of the functional images out of many functional images. A plurality of these blended functional images and blended functional images projected onto the tomogram can be simultaneously displayed on a screen.

According to the embodiment 1 described above, pixels indicating values greater than a threshold value in the functional image are estimated and displayed as a characteristic region such as a ischemic region. By using a plurality of parameters of the functional image, it is allowed to increase the information for diagnosis. Upon displaying the characteristic portion in colors that differ depending upon the parameters, it can be learned at a glance which parameter is representing what kind of abnormal condition at which region. Upon displaying them in an overlapped manner, it can be learned at a glance that there is occurring an abnormal condition of a plurality of parameters at a certain region.

The color density and coloring can be varied depending upon the magnitude of the pixel values in the characteristic region that is colored, and the degree of abnormal condition can be judged.

The transparency of the characteristic region is variable which allows the operator to switch to a screen where the target region can be easily recognized. Besides, the outer periphery of the characteristic region and a region that is to be diagnosed are selected on the image and are displayed as ROI being colored as described above without disturbed by undesired data.

Upon being overlapped on the tomogram 40 as shown in FIG. 8, further, a positional relationship can be easily grasped relative to the outer region such as the skull to facilitate the diagnosis. Further, any arrangement can be selected such as displaying the functional images in parallel, overlapped or partly overlapped to meet the requirement of diagnosis and user's intention. Further, the functional image chiefly uses CBF, CBV and MTT, and their measured values can be confirmed on the screen at the same time. Upon recording ROI, threshold value and arrangement for forming the characteristic portion, the diagnosis can be repeated at any time under the same conditions making it easy to compare the functional images before and after the surgical operation or therapy and to measure the effect of surgical operation or therapy without permitting subjectivity of the operators.

Moreover, differential images before and after the therapy can be displayed, too.

Embodiment 2

Embodiment 2 utilizes the constitution of FIG. 1 like in the embodiment 1. The constituent elements are as described in the embodiment 1 and their description is not repeated. In the embodiment 2, too, the image processing apparatus 2 is, for example, a computer mounting a program for controlling the data collection means 1, a program for forming a tomogram, such as reconstituting the image, a program for analyzing and mapping the biological function data, and a program for forming a composite image. The above programs may be mounted in one computer or may be mounted in a divided manner in a plurality of computers depending upon the kinds of operations.

Figure 9:
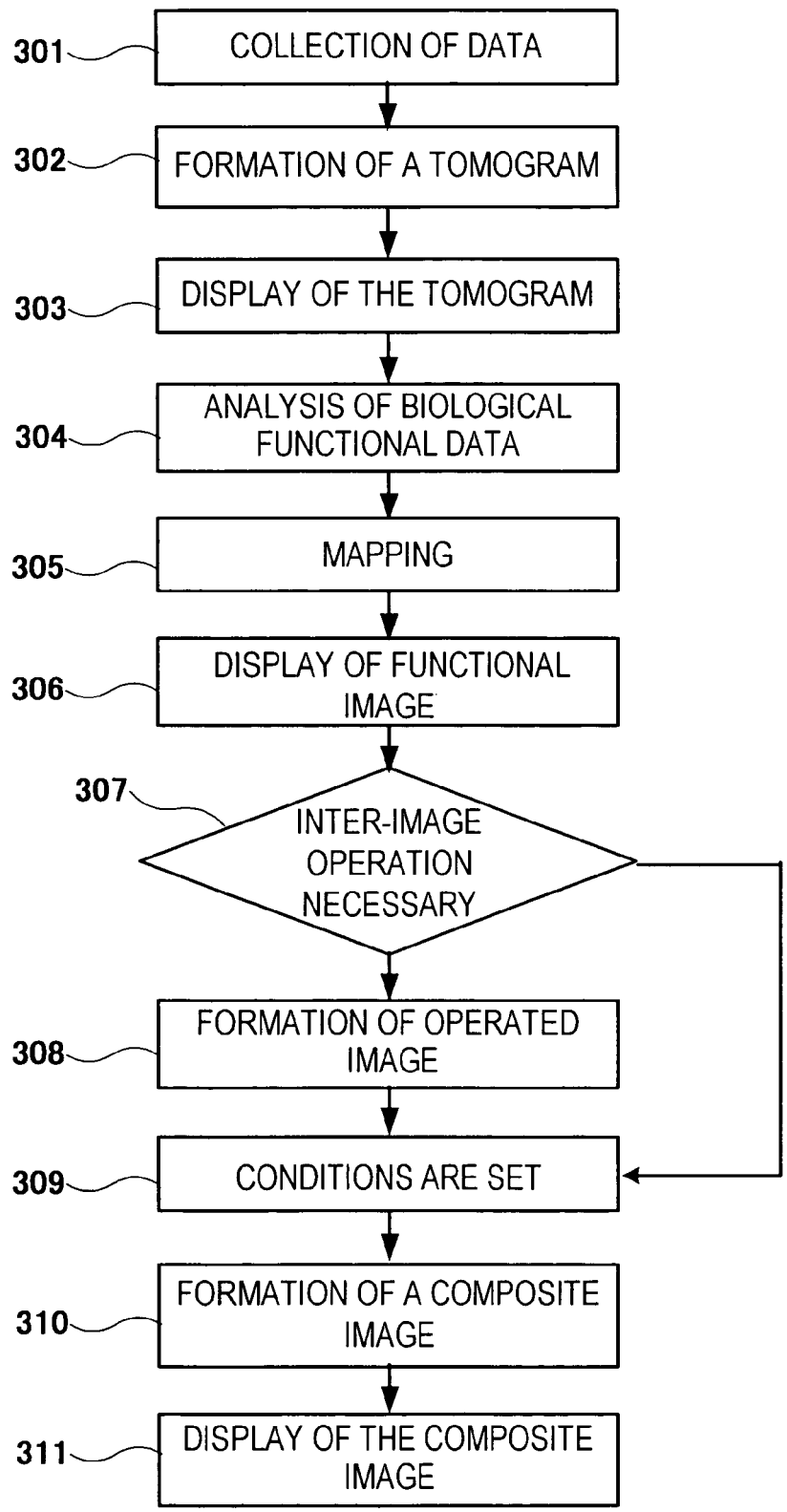
FIG. 9 is a flowchart from collecting the data up to displaying a composite image according to an embodiment 2 of the invention.

FIG. 9 is a flowchart from collecting the data through up to displaying a composite image using a program in the image diagnosing apparatus according to the embodiment. The process according to the embodiment will now be described according to the flowchart. At step 301, acquisition means 1 (see FIG. 1) controlled by a control program mounted on the computer 2 collects X-ray attenuation signals and echo signals emitted from nuclear magnetic resonance.

When, for example, the collection apparatus is a CT apparatus, and the biological function data to be analyzed are perfusion data of the brain tissue, a contrast-emphasizing substance such as an iodine-type contrast medium is injected to the patient 5, and dynamic imaging is effected to collect the data necessary for the analysis of the biological function data.

At step 302, a tomogram is formed by using a program such as reconstituting the image mounted on the computer 2. The tomogram may be on any cross section such as axial, coronal or sagittal. At step 303, the tomogram formed at step 302 is displayed. At step 304, a parameter representing the biological function data is calculated by using a program for analyzing the biological function data mounted on, for example, the computer 2. It is desired that the parameter is calculated for each pixel of the tomogram from the standpoint of preventing a decrease in the resolution. However, when it is necessary to finish the operation within a short period of time such as quickly diagnosing the biological function data, the operation may be executed while reducing the image or the operation may be executed for each of the pixels. At step 305, a functional image is formed by mapping the results of operation obtained at step 304 by using a mapping program mounted on the computer 2. At step 306, the functional image formed at step 305 is displayed on the display means 4. Here, at step 306, not only the functional image is displayed but, as required, the functional image and the tomogram may be displayed together.

At step 307, the operator selects if it is necessary to effect the image operation such as the subtraction operation. If it is not necessary, the routine proceeds to step 309. When it is desired to emphasize the region where the biological function data are significantly changing through the examination of a plurality of times, it is desired to execute the image operation such as subtraction operation.

When the necessity of image operation is selected at step 307, the operator selects if the quantitative values need to be corrected. If it is not necessary, the routine proceeds to step 308. In the brain perfusion image, for example, it may often happen, depending upon the imaged cross section, that the partial volume effect is not properly corrected, which is a phenomenon in which the CT value is not correctly calculated in a region of a high CT value in the tomogram and, particularly, in the major artery along the slice due to the presence of a substance of a low CT value spanning across the imaged slice, and the quantitative value is excessively evaluated. In such a case, it is desired to effect the image operation after having corrected the quantitative values. At step 308, the quantitative values are corrected by using a program for correcting quantitative values mounted on the computer 2 when it is necessary to correct the quantitative values. At step 308, further, the operated image is formed by using an image operation program mounted on the computer 2. The image operation at step 308 may be any operation such as subtraction operation. At step 309, there are set the regional conditions for the operated image or the functional image for composite with the tomogram.

This step, however, is not necessary when the whole region of the operated image or the functional image is to be overlapped on the tomogram so as to be composed therewith. When the operated image or a particular region only of the functional image is to be overlapped on the tomogram so as to be composed, the threshold value or ROI is set, or only those pixels are selected that satisfy any conditional formula to specify a region for overlapping. When, for example, it is desired to display only a region exhibiting a conspicuous change in the right semi-sphere in a case where the operated image is a differential image of the cerebral perfusion functional image in the examination of a plural number of times, the ROI may specify the whole right semi-sphere and only those pixels of which the pixel values P satisfy the conditions of the following formula 5 may be overlapped on the tomogram and composed.

$$P = \text{Mean} + k \cdot \text{SD} \tag{5}$$

In the above formula, Mean is an average value of all pixel values of the operated image, SD is a standard deviation, and k is any real number.

When, for example, it is desired to display a change in the abnormal region with the passage of time in a case where the functional image is a cerebral perfusion functional image in the examination of a plural number of times, only those pixels having pixel values smaller than a threshold value or larger than the threshold value are overlapped on the tomogram and are composed.

At step 310, a composite image is formed by using a program for forming composite image mounted on the computer 2. Formation of the composite image will be described later in detail. At step 311, a composite image is displayed on the display means 4. Here, at step 311, not only the composite image is displayed but, as required, the composite image and the functional image, the operated image and the tomogram may be displayed together. At this moment, the number of pixels in the region that is set and composed at step 309, average numbers, standard deviation and histogram, may also be displayed to offer the data further useful for the analysis of the biological function data.

When the X-ray attenuation data and the susceptibility signal intensity data have been collected already, the X-ray attenuation data and the susceptibility signal intensity data are read out from storage means 5 such as a hard disk contained in the computer 2 or attached to the outer side thereof, and step 302 and subsequent steps are executed. Further, when the tomogram has been formed already, the tomogram is readout from the storage means 5 such as hard disk incorporated in the computer 2 or attached to the outer side thereof, and step 303 and subsequent steps are executed. When the functional image has been formed already, the functional image is readout from the storage means 5 such as a hard disk incorporated in the computer 2 or attached to the outer side thereof. Or, as required, the functional image and the tomogram are read out and, then, step 306 and subsequent steps are executed.

Next, described below in detail concerning step 308 is how to form a new image for diagnosis by operating a plurality of functional images obtained through the examination of a plural number of times. When a change of the biological function data is observed in the examination of a plural number of times, for example, the functional image may be subtracted in the examination of a plural number of times. The kind of operation is not limited to the subtraction operation but may be an addition, a multiplication, a division or a combination of any arithmetic operations depending upon the use. The inter-image operation may be carried out with all the pixels of the image on every pixel.

Figure 10:
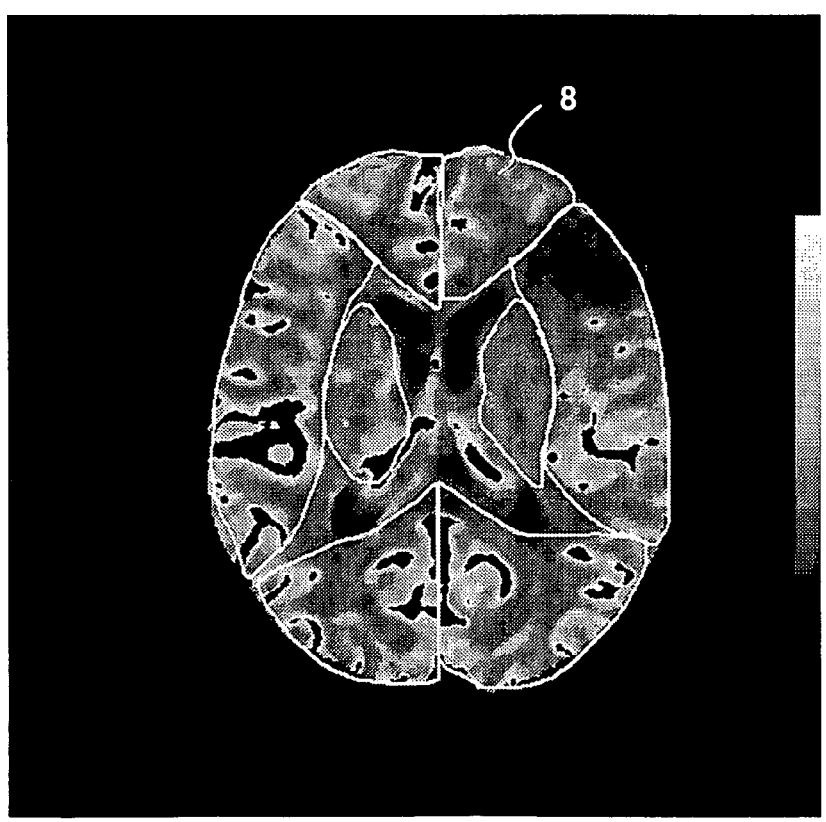
FIG. 10 is a view illustrating how to set ROI at the time of image operation in the embodiment 2 of the invention.

As required, further, the operation may be effected for each region surrounded by ROI8 that is arbitrarily set as shown in FIG. 10, or characteristic quantities such as an average value, an intermediate value, a maximum value and a minimum value may be operated in the region ROI. This makes it possible to conduct visual evaluation in a size that can be easily diagnosed.

Further, an equivalent line may be drawn to divide the functional image into several regions and to operate the divided regions. When the functional image is, for example, a cerebral perfusion image, an equivalent line may be drawn to divide the image into a white matter, a gray matter and a blood vessel bed. By specifying ROI, further, the functional image can be divided into anatomical segments such as thalamus, nucleus lentiformis and corpus callosum. Executing the inter-image operation for each of the anatomical segments is effective in evaluating a change in the biological function data.

Next, described below concerning step 308 is how to correct the quantitative values. In the cerebral perfusion image, for example, quantitative stability is obtained by correcting the partial volume effect as described in the embodiment 1 based upon a maximum value of a time-concentration curve or on the area under the curve in the superior sagittal sinus. Depending upon the imaged section, however, the superior sagittal sinus may not be included in the imaged section. In such a case, the partial volume effect cannot be properly corrected, and the quantitative value becomes incorrect. If there is an image from which it can be judged that the partial volume effect was properly corrected in the examination of a plural number of times, the quantitative value in other examinations is corrected by using a correction parameter (maximum value or area under the curve) in the examination.

As another correction method, there is a method of correction based upon an average value in the healthy region. This is a method presuming that the biological function data in the healthy region of the same person being examined remain stable irrespective of the date of examination. An average quantitative value in the healthy region on a functional image in an examination is denoted by Mean 1, and an average quantitative value in the healthy region on a functional image in another examination is denoted by Mean 2. Here, the pixel values (quantitative values) of either functional image are shifted so that Mean 1 is brought into agreement with Mean 2, thereby to correct the quantitative values.

Next, described below concerning step 310 is how to form a composite image (hereinafter called blended functional image projected onto a tomogram) of the operated image or the functional image and the tomogram. In this embodiment, the number of color gradations is M. The number M of gradations is a positive integer and can be arbitrarily set to be 8 bits (256 gradations), 12 bits (4,096 gradations), 16 bits (65,536 gradations) and 32 bits (4,294,967,296 gradations). The gradation that can be displayed becomes abundant with an increase in the number of gradations. The color gradations, usually, include those of hue, brightness and chroma, and exist in many kinds.

In forming a composite image, a conversion coefficient C is calculated based on a pixel value P of the operated image or the functional image, display window value WL and display window width WW. The conversion coefficient C is determined as given, for example, by the formula 1 and as shown in FIG. 3 like in the embodiment 1. In this embodiment, a section from (WL−WW/2) to (WL+WW/2) was linearly converted, which, as required, however, may be non-linearly converted arbitrarily. Further, the pixel value may be used directly as the conversion coefficient.

FIG. 4 illustrates look-up tables (LUTs) used for forming a composite image. The LUT referred to in this embodiment is a correspondence table between the conversion coefficient C described above and the components (e.g., component R, component G, component B) of the displayed color. If the components of the darkest pixel in the display window, i.e., the components R, G, B of the darkest color (lower end color) having a conversion coefficient of not greater than WL−WW/2 are denoted by R1, G1, B1, the components of the brightest pixel in the display window, i.e., the components R, G, B of the brightest color fitted to the pixel having a conversion coefficient of not smaller than WL+WW/2 are denoted by Rh, Gh Bh, then, the components R(C), G(C), B(C) of R, G, B of LUT using the conversion coefficient C are determined as given by, for example, the formula 2 and as shown in FIG. 5.

In the example shown in FIG. 5, the components from the darkest color (lower end color) to the brightest color (upper end color) were connected together linearly, which, however, may be connected in any non-linear shape, as required. When there are a plurality of parameters indicating the biological function data and a plurality of functional images corresponding to the plurality of parameters, there can be formed a plurality of operated images. When there are M pieces of operated images, functional images or M pieces of operated images and functional images, it is desired to set look-up tables of a number of M corresponding to an operated image 1 (or a functional image 1), an operated image 2 (or a functional image 2), - - -, an operated image M (or a functional image M), i.e., to set LUT1, LUT2, - - -, LUTM. However, the same look-up table may be used in common among the plurality of operated images or the functional images.

Next, displaying a composite image at step 311 will be described in detail. If the components of a color displayed on a pixel (i, j) of the composite image are denoted by RTF(i, j), GTF(i, j) and BTF(i, j), these components are determined according to the formula 4.

Here, WB is a weight of the operated image or the functional image, WT is a weight of the tomogram, and CC(i, j) is a conversion coefficient of the tomogram at the pixel (i, j) and is determined in the same manner as that of finding the conversion coefficient of the above operated image or the functional image.

RT(CC(i, j)), GT(CC(i, j)) and BT(CC(i, j)) are the component values of R, G and B specified in the look-up table LUTT for tomogram using a conversion coefficient CT(P). When the tomogram is to be displayed on a gray scale, the look-up table LUTT for tomogram may be set as shown in, for example, FIG. 6. When the tomogram is to be displayed in color, tables of RGB are necessary as shown in FIG. 5. Further, RF(i, j), GF(i, j) and BF(i, j) are parameters determined based on a ratio of composing the operated image or the functional image, and are determined according to the formula 3.

Here, Wk is a weight for composing the operated image k or the functional image k, and Ck(i, j) is a conversion coefficient for the operated image k or the functional image k at the pixel (i, j). Moreover, Rk(Ck(i, j)), Gk(Ck(i, j)) and Bk(Ck(i, j)) are the component values of R, G and B defined in LUTk using the conversion coefficient Ck(i, j). Here, k is an integer of 1 to M, M being in agreement with the number of pieces of the operated images or the functional images. When there is only one piece of the operated image or the functional image, the formula 4 is to be calculated as the formula 6.

$$RTF(i, j) = \frac{RF(CF(i, j)) \cdot WB + RT(CC(i, j)) \cdot WT}{WB + WT} \quad (6)$$

$$GTF(i, j) = \frac{GF(CF(i, j)) \cdot WB + GT(CC(i, j)) \cdot WT}{WB \cdot WT}$$

$$BTF(i, j) = \frac{BF(CF(i, j)) \cdot WB + BT(CC(i, j)) \cdot WT}{WB + WT}$$

Here, Ck(i, j) represents a conversion coefficient of the operated image or the functional image at the pixel (i, j). To form a composite image of the operated image or the functional image and the tomogram, RTF(i, j), GTF(i, j) and BTF(i, j) are determined according to the formula 4 or the formula 6 in the case of the pixel displayed on the gradation color scale. For a pixel displayed in a particular color, RTF(i, j), GTF(i, j) and BTF(i, j) are determined by setting the weight WB to 0 in the formula 4 or the formula 6. This is effected for all pixels which are, then, mapped according to RTF(i, j), GTF(i, j) and BTF(i, j).

The region (particular region) displayed on the gradation color scale may be set depending upon a threshold value set through the console 4, any conditional formula and ROI. The threshold value, conditional formula and ROI are set in a number of one or in a plural number for each of the images that have been operated. After the operation, if the pixel value at a pixel (i, j) of the image k or the functional image k lies within a range set by the threshold values for the operated image k or the functional image k and by the conditional formula and if the pixel (i, j) lies within a range set by ROI, the components Rk(Ck(i, j)), Gk(Ck(i, j)) and Bk(Ck(i, j)) are determined according to the setting method of LUT mentioned above. If the pixel value lies outside the range, a particular arbitrary value is assigned to the components Rk(Ck(i, j)), Gk(Ck(i, j)) and Bk(Ck(i, j)).

By effecting the above processing for all pixels, particular region only is displayed on the gradation color scale in the operated image or the functional image. Other regions are displayed in a particular color, i.e., displayed by the CT tomogram 40 only in black or gray shown in, for example, FIGS. 7 and 8 and FIGS. 11 to 18. The above processing is effected for all operated images or functional images. If M pieces of operated images or functional images need not all be composed, the composite may be effected by setting the weight to 0 in the operated images or the functional images that need not be composed.

In composing the image, when it is desired to vary the degree of emphasis of data obtained from an operated image k or a functional image k, Wk in the formula 5 may be varied based upon the parameters input from the console 4.

In composing the image, when it is desired to vary the region that is displayed on the gradation color scale, the threshold value, conditional formula and ROI may be varied based upon the parameters input from the console 4.

In composing the image, when it is desired to vary the degree of emphasis of the operated image, functional image or tomogram, WB and WT in the formula 4 or the formula 6 may be varied based upon the parameters input from the console 4.

Figure 11:
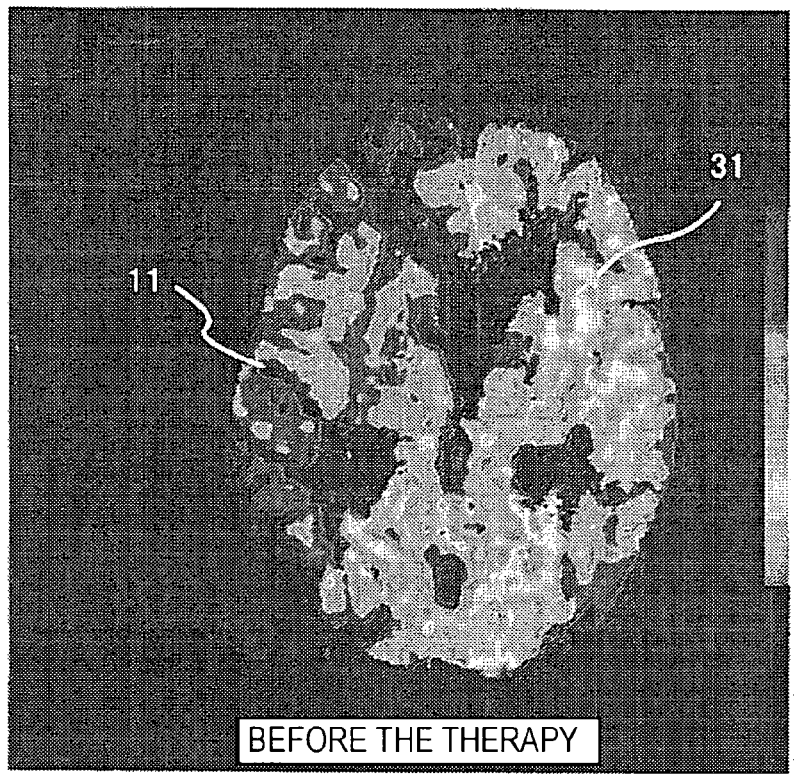
FIG. 11 is an MTT functional image before the therapy according to an embodiment 2 of the invention.
Figure 12:
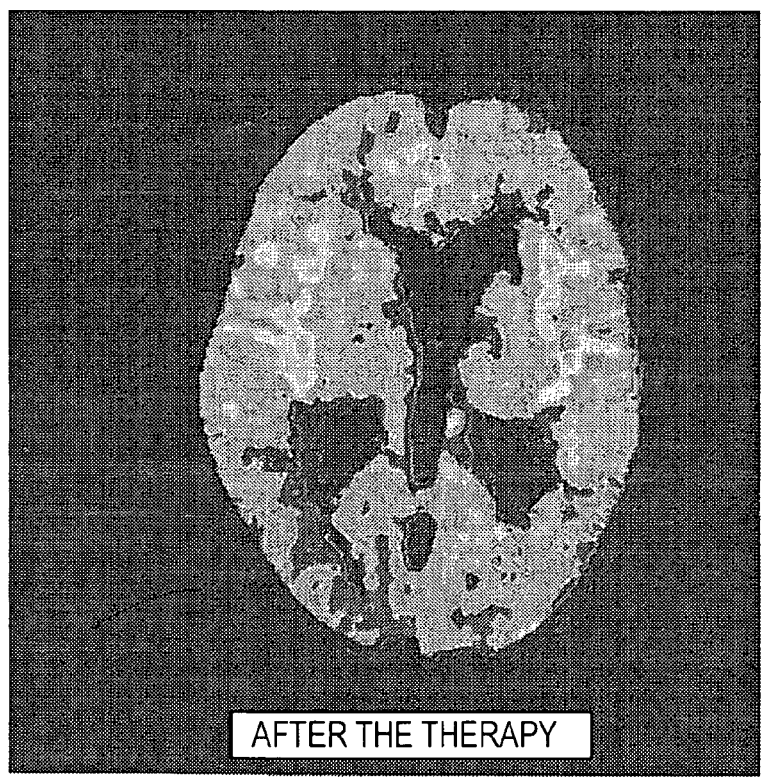
FIG. 12 is an MTT functional image after the therapy in the embodiment 2 of the invention.
Figure 13:
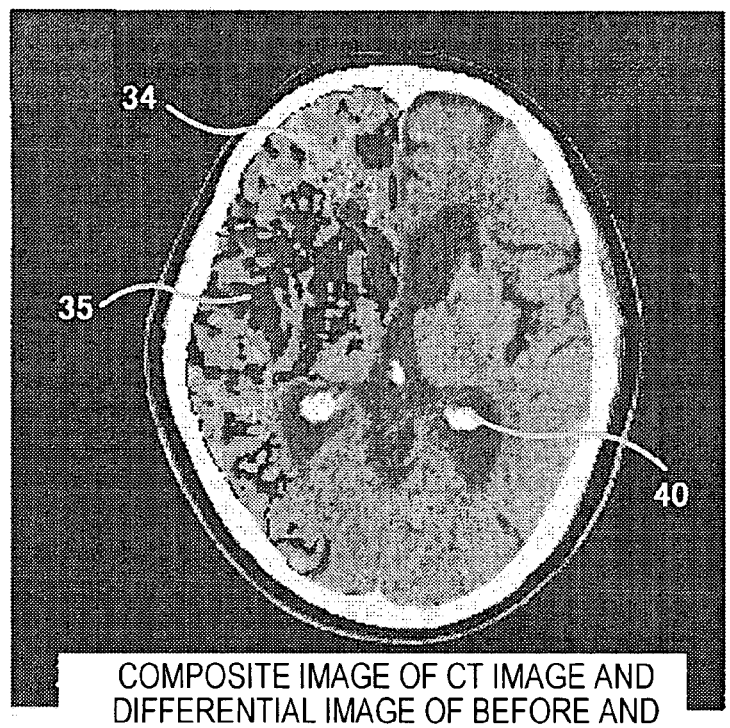
FIG. 13 is an image formed by composing a CT tomogram and MTT differential images before and after the therapy in the embodiment 2 of the invention.

FIGS. 11 to 18 illustrate examples in which the invention is applied to the cerebral perfusion functional images formed from the CT images. FIGS. 11 to 13 are sample images forming composite images of CT images and differential images of mean transit time images MTT of before and after the therapy of a patient suffering from the right internal carotid artery stenosis. In these samples, only those regions where the mean transit time MTT is significantly changing are displayed on a color gradation scale of rainbow colors. In the regions where the mean transit time MTT is significantly changing, WB in the formula 5 is set to 0.8 and WT is set to 0.2 to effect the synthesis. In other regions, WB is set to 0 and WT is set to 1 to effect the synthesis. In FIG. 13, reference numeral 34 denotes a portion displayed in a warm color and where the MTT is changing relatively greatly, 35 denotes a portion displayed in a cold color and where the MTT is changing relatively little, and 40 denotes a region of the tomogram only displayed on a gray scale. Here, color is allocated depending upon the magnitude of difference between FIG. 11 and FIG. 12.

FIGS. 11, 12 and FIGS. 14 to 16 are sample images forming differential images of mean transit time images MTT, differential images of cerebral blood volume images CBV and composite images of CT images of a patient suffering from the right internal carotid artery stenosis before and after the therapy. In these sample images, the regions where the cerebral blood volume image CBV is significantly changing are displayed on a color gradation scale 36 of blue color, and the regions where the mean transit time MTT is significantly changing are displayed on a color gradation scale 37 of red color. Further, the composite is effected while setting W1 (i.e., weight of a differential image of the cerebral blood volume image) in the formula 3 to be 0.75 and setting W2 (i.e., weight of a differential image of the mean transit time image) to be 0.25. Further, in a region where the cerebral blood volume CBV or the mean transit time MTT is significantly changing, the composite is effected by setting WB to be 0.8 and setting WT to be 0.2 in the formula 4. In other regions, the composite is effected by setting WB to 0 and WT to 1.

FIGS. 11 to 13 illustrate examples of when there is only one piece of the operated image or the functional image, and FIGS. 11, 12, 14 to 16 illustrate examples of when there are two pieces of operated images or functional images. The invention can be similarly applied even when there are three or more pieces of operated images or functional images. These sample images make it possible to easily grasp a change with the lapse of time in a region where a conspicuous change has occurred in the biological function data or in the diseased region without leaving uncertainty in the ROI setting that may be caused by the preconception of the operator and without spoiling the shape inherent in the examined region. According to this embodiment as described above, there is no room for inviting uncertainty in the ROI setting caused by the preconception of the operator, or for spoiling the shape inherent in the examined region, while making it possible to easily grasp a change with the lapse of time in a region where a conspicuous change has occurred in the biological functional data or in the diseased region.

According to the present invention as described above, data obtained from the tomogram and the data obtained from a plurality of functional images, can be obtained from a piece of image making it easy to judge the degree of ischemia in the biological function disorder.

Figure 14:
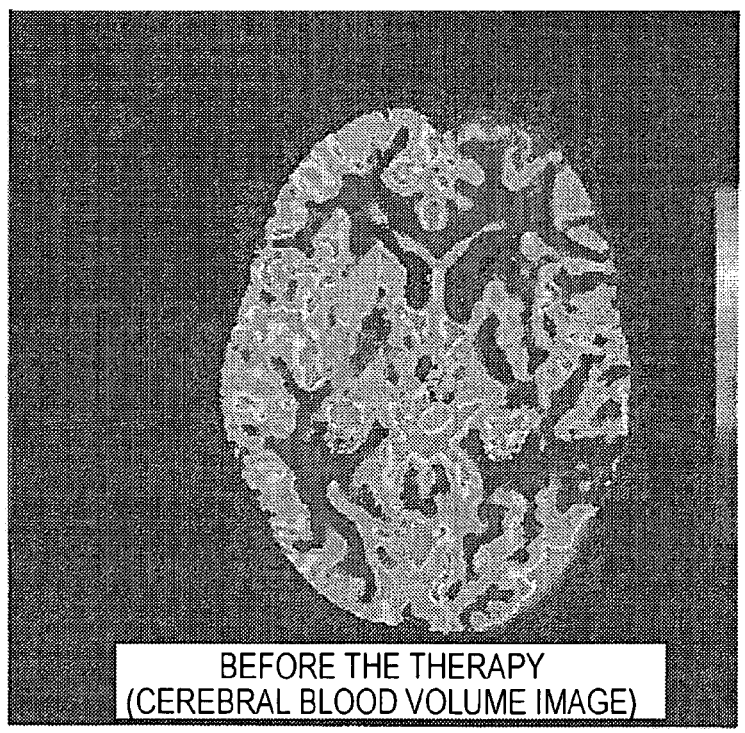
FIG. 14 is a CBV functional image before the therapy.
Figure 15:
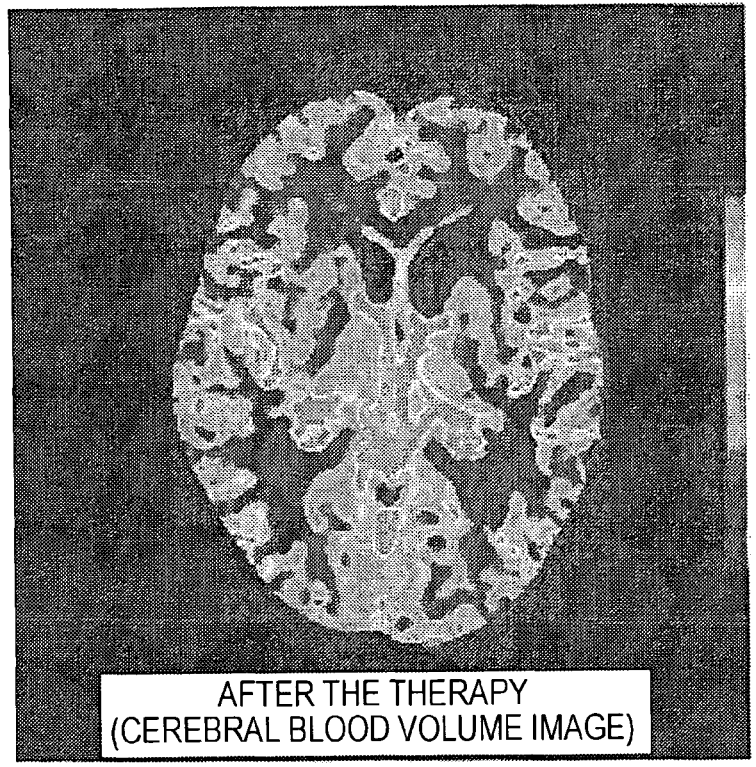
FIG. 15 is a CBV functional image after the therapy.
Figure 16:
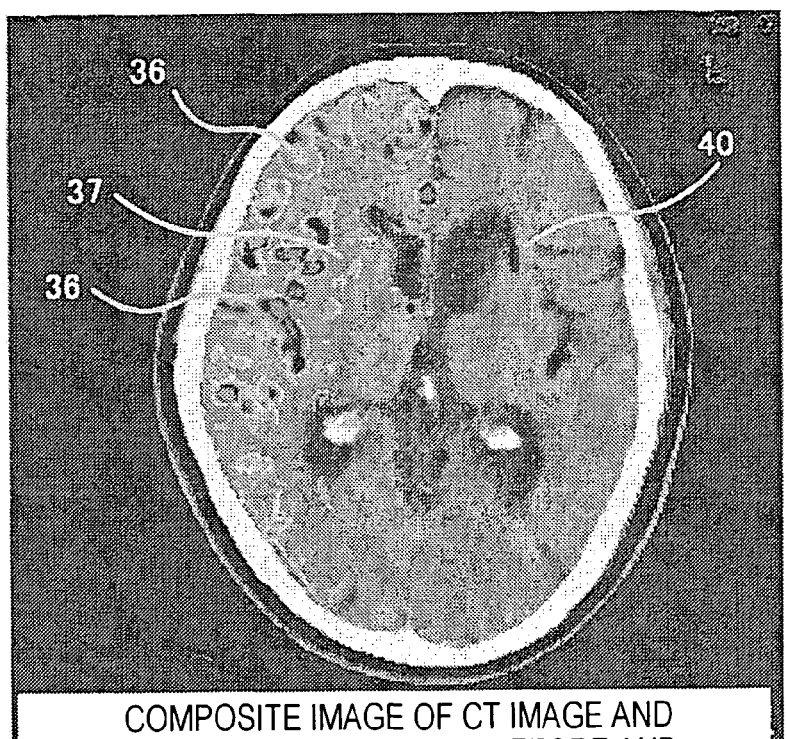
FIG. 16 is an image formed by composing CBV and MTT differential images before and after the therapy and the CT tomogram concerning FIGS. 11, 12, 14 and 15.

FIG. 2
201—COLLECTION OF DATA
202—FORMATION OF A TOMOGRAM
203—DISPLAY OF THE TOMOGRAM
204—ANALYSIS OF BIOLOGICAL FUNCTION DATA
205—MAPPING
206—DISPLAY OF IMAGE
207—FORMATION OF COMPOSITE IMAGE
208—DISPLAY OF IMAGE
FIG. 3
1—CONVERSION COEFFICIENT C
2—PIXEL VALUE P
PMAX—MAXIMUM PIXEL VALUE
CMAX—MAXIMUM CONVERSION COEFFICIENT VALUE
FIG. 4
LUT FOR FUNCTIONAL IMAGE 1
Conversion Coefficient C
LUT FOR FUNCTIONAL IMAGE 2
Conversion Coefficient C
LUT FOR FUNCTION IMAGE M
CONVERSION COEFFICIENT C
FIG. 5
1—CONVERSION COEFFICIENT
Rl—MINIMUM COMPONENT R
Rh—MINIMUM COMPONENT R
Gl—MINIMUM COMPONENT G
Gh—MINIMUM COMPONENT G
Bl—MINIMUM COMPONENT B
Bh—MINIMUM COMPONENT B
CMAX—MAXIMUM CONVERSION COEFFICIENT
FIG. 6
LUT FOR TOMOGRAM
CONVERSION COEFFICIENT C
FIG. 9
301—COLLECTION OF DATA
302—FORMATION OF A TOMOGRAM
303—DISPLAY OF THE TOMOGRAM
304—ANALYSIS OF BIOLOGICAL FUNCTION DATA
305—MAPPING
306—DISPLAY OF FUNCTION IMAGE
307—IMAGE OPERATION NECESSARY
308—FORMATION OF OPERATED IMAGE
309—CONDITIONS ARE SET
310—FORMATION OF A COMPOSITE IMAGE
311—DISPLAY OF THE COMPOSITE IMAGE
FIG. 11
BEFORE THE THERAPY
FIG. 12
AFTER THE THERAPY
FIG. 13
COMPOSITE IMAGE OF CT IMAGE AND DIFFERENTIAL IMAGE OF BEFORE AND AFTER THE THERAPY
FIG. 14
BEFORE THE THERAPY (CEREBRAL BLOOD VOLUME IMAGE)
FIG. 15
AFTER THE THERAPY (CEREBRAL BLOOD VOLUME IMAGE)
FIG. 16
COMPOSITE IMAGE OF CT IMAGE AND DIFFERENTIAL IMAGE OF BEFORE AND AFTER THE THERAPY

The invention claimed is:

1. An apparatus for displaying image, said apparatus comprising:
an acquisition part configured to collect CT or MR head image data of a person being examined;
a tomogram forming part configured to form a tomogram from said CT or MR head image data;
an analysis part configured to calculate at least one biological function data in said tomogram, formed based on said CT or MR head image data, regarding temporal changes in values of the same pixels or section of an organ with passage of time;
a functional image forming part configured to form two or more functional images based on said biological function data;
a composite image forming part configured to form a composite image by composing said tomogram and a blended image obtained by composing two or more portion images extracted from said functional images; and
a display part configured to display said tomogram and said blended image, overlapping each other;
wherein said two or more portion images extracted from said functional images have different respective gradation colors, as compared to each other, and are overlapped in display.

2. An apparatus according to claim 1, wherein said composite image forming part is configured to form a composite image by composing said tomogram and an operated image obtained by performing an intra-image operation on said functional images together.

3. A method of displaying image, said method comprising:
a step of collecting CT or MR head image data of a person being examined;
a step of forming a tomogram from said CT or MR head image data;
a step of calculating at least one biological function data in said tomogram, formed based on said CT or MR head image data, regarding temporal changes in values of the same pixels or section of an organ with passage of time;
a step of forming two or more functional images based on said biological function data;
a step of forming a composite image by composing said tomogram and a blended image obtained by composing portion images extracted from said functional image; and
a display step of displaying said tomogram and said blended image, overlapping each other;
wherein said two or more portion images extracted from said functional images have different respective gradation colors, as compared to each other, and are overlapped in display, the respective gradation colors of the two or more portion images corresponding to the evaluated value of said biological function data, and
other regions in said functional images are displayed in an arbitrary color different form the respective gradation colors of the two or more portion images, or are displayed transparently.

4. A method of displaying image according to claim 3, wherein the step of forming said functional image sets to zero the ratio of said functional image in other regions in said functional image.

5. A method of displaying image according to claim 3, further comprising arbitrarily varying the gradation color allocated to said biological function data image.

6. A method of displaying image according to claim 3, further comprising arbitrarily setting the ratios of the functional images in said synthetic images and of said tomogram.

7. A method of displaying image according to claim 3, wherein the step of forming said functional image specifies part of the regions in said functional image depending upon whether the image data value of said pixel unit lies inside or outside a predetermined range.

8. A method of displaying image according to claim 3, wherein the step of forming said functional image determines an arbitrary interested region in said functional image as region of interest in said functional image.

9. A method of displaying image according to claim 3, wherein the step of forming said functional image renders the pixel values of the pixels of the image data on a predetermined display window value level and in a predetermined display window width to be corresponded to conversion coefficients, and determines said gradation color based on the conversion coefficients.

10. A method of displaying image according to claim 9, wherein the step of forming said functional image determines the gradation color allocated to said functional image depending upon the pixel values of the pixels of the image data for each of RGB and upon various look-up tables to which the conversion coefficients are corresponded.

11. A functional image display apparatus comprising:
an acquisition part configured to collect CT or MR head image data of a person being examined;
a tomogram forming part configured to form a tomogram from the CT or MR head image data;
an analysis part configured to calculate at least one biological function data in said tomogram, formed based on said CT or MR head image data, regarding temporal changes in values of the same pixels or section of an organ with passage of time;
a functional image forming part configured to form two or more functional images based on the biological function data;
a composite image forming part configured to form a composite image by composing the tomogram and a blended image obtained by composing portion images extracted from the functional images; and
a display part configured to display the tomogram and the blended image, overlapping each other;
wherein said two or more portion images extracted from said functional images have different respective gradation colors, as compared to each other, and are overlapped in display, the respective gradation colors of the two or more portion images corresponding to the evaluated value of the biological function data; and
wherein other regions in the functional images are displayed in an arbitrary color different form the respective gradation colors of the two or more portion images, or are displayed transparently.

12. An apparatus according to claim 11, wherein said composite image is displayed by any one of a parallel display or a partial display.

13. An apparatus according to claim 11, wherein said functional image forming part sets to zero a ratio of said functional image in other regions in said functional image.

14. An apparatus according to claim 11, wherein said functional image forming part arbitrarily varies the gradation color allocated to said biological function data.

15. An apparatus according to claim 11, wherein said functional image forming part arbitrarily set ratios of the functional images in said composite images and of said tomogram.

16. An apparatus according to claim 11, wherein said functional image forming part specifies part of the regions in said functional image depending upon whether the image data value of said pixel unit lies inside or outside a predetermined range.

17. An apparatus according to claim 11, wherein said functional image forming part determines an arbitrary interested region in said functional image as region of interest in said functional image.

18. An apparatus according to claim 11, wherein said functional image forming part renders the pixel values of the pixels of the image data on a predetermined display window value level and in a predetermined display window width to be corresponded to conversion coefficients, and determines said gradation color based on the conversion coefficients.

19. An apparatus according to claim 18, wherein said functional image forming part determines the gradation color allocated to said functional image depending upon the pixel values of the pixels of the image data for each of RGB and upon various look-up tables to which the conversion coefficients are corresponded.

20. An apparatus according to claim 11, wherein said biological function data is at least one of the blood flow function data as represented by blood volume, blood flow and mean transit time.

21. The functional image display apparatus of claim 11, wherein the biological function data is perfusion data of brain tissue.

* * * * *